(12) United States Patent
Hase

(10) Patent No.: US 12,167,851 B2
(45) Date of Patent: Dec. 17, 2024

(54) TREATMENT INSTRUMENT

(71) Applicant: Olympus Corporation, Tokyo (JP)

(72) Inventor: Hidenosuke Hase, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 18/056,687

(22) Filed: Nov. 17, 2022

(65) Prior Publication Data
US 2023/0082517 A1 Mar. 16, 2023

Related U.S. Application Data

(63) Continuation of application No. PCT/JP2020/021673, filed on Jun. 1, 2020.

(51) Int. Cl.
*A61B 17/29* (2006.01)
*A61B 17/072* (2006.01)

(52) U.S. Cl.
CPC ..... *A61B 17/07207* (2013.01); *A61B 2017/2927* (2013.01)

(58) Field of Classification Search
CPC ...... A61B 17/07207; A61B 2017/2927; A61B 18/1445; A61B 2017/00477; A61B 2017/2929; A61B 2018/00589; A61B 2018/0063; A61B 2018/00994; A61B 17/320068

(Continued)

(56) References Cited

U.S. PATENT DOCUMENTS 3,069,875 A * 12/1962 Crum, Jr. ............... F16D 1/101
464/169
3,211,485 A * 10/1965 Petersen ................. F16D 1/10
464/57

(Continued)

FOREIGN PATENT DOCUMENTS

| JP | 2008178688 A | 8/2008 |
| JP | 2014236984 A | 12/2014 |

(Continued)

OTHER PUBLICATIONS

"International Application Serial No. PCT/JP2020/021673, International Search Report dated Aug. 4, 2020", (Aug. 4, 2020), 3 pgs.

*Primary Examiner* — Robert F Long
(74) *Attorney, Agent, or Firm* — Schwegman Lundberg & Woessner, P.A.

(57) ABSTRACT

A treatment tool includes: an end effector configured to implement treatment of living tissue; an operation input portion configured to receive operation; a tubular portion provided along a longitudinal axis of the treatment tool, the tubular portion having a first end and a second end, the first end being connected to the end effector, the second end being provided with a first engagement portion; a driver configured to move along the longitudinal axis according to the operation on the operation input portion, the driver including a second engagement portion configured to engage with the first engagement portion; and a pusher configured to connect the tubular portion and the driver to each other by coming into contact with the tubular portion toward a central axis of the tubular portion in a state where the first engagement portion and the second engagement portion have engaged with each other.

19 Claims, 11 Drawing Sheets

(58) Field of Classification Search
USPC .......................................... 227/175.1–182.1
See application file for complete search history.

(56) References Cited

U.S. PATENT DOCUMENTS

| | | | | |
|---|---|---|---|---|
| 3,823,474 | A * | 7/1974 | Ionescu | B27B 17/0008 16/436 |
| 4,179,632 | A * | 12/1979 | Harvell | H02K 7/145 403/324 |
| 4,971,161 | A * | 11/1990 | Godell | B25F 3/00 175/18 |
| 5,151,101 | A | 9/1992 | Grossi et al. | |
| 5,163,598 | A * | 11/1992 | Peters | A61B 17/0686 227/176.1 |
| 5,695,504 | A * | 12/1997 | Gifford, III | A61B 17/12045 606/139 |
| 6,006,434 | A * | 12/1999 | Templeton | A01D 34/90 30/296.1 |
| 6,056,735 | A | 5/2000 | Okada et al. | |
| 6,305,867 | B1 * | 10/2001 | Schweigert | F16D 1/101 403/14 |
| 6,938,587 | B2 | 9/2005 | Thomas | F02B 63/02 30/276 |
| 7,739,800 | B2 * | 6/2010 | Hurley | A01D 34/905 172/14 |
| 8,333,721 | B2 * | 12/2012 | Makin | A61B 8/4488 601/3 |
| 8,453,914 | B2 * | 6/2013 | Laurent | A61B 17/320016 227/179.1 |
| 8,490,852 | B2 * | 7/2013 | Viola | A61B 17/128 227/179.1 |
| 9,795,380 | B2 * | 10/2017 | Shelton, IV | A61B 17/105 |
| 9,955,966 | B2 * | 5/2018 | Zergiebel | A61B 17/07207 |
| 9,980,730 | B2 * | 5/2018 | Sgroi | A61B 17/1155 |
| 10,022,126 | B2 * | 7/2018 | Sgroi, Jr. | A61B 17/1155 |
| 10,039,549 | B2 * | 8/2018 | Williams | A61B 17/1155 |
| 10,085,744 | B2 * | 10/2018 | Williams | A61B 17/068 |
| 10,117,655 | B2 * | 11/2018 | Scirica | A61B 17/068 |
| 10,117,656 | B2 * | 11/2018 | Sgroi, Jr | A61B 17/1155 |
| 10,130,364 | B2 * | 11/2018 | Beaupré | F16D 41/16 |
| 10,285,694 | B2 * | 5/2019 | Viola | A61B 17/072 |
| 10,314,581 | B2 * | 6/2019 | Campbell | A61B 17/07207 |
| 10,478,185 | B2 * | 11/2019 | Nicholas | A61B 17/07207 |
| 10,765,442 | B2 * | 9/2020 | Strobl | A61B 17/29 |
| 10,874,393 | B2 * | 12/2020 | Satti, III | A61B 17/320016 |
| 10,973,518 | B2 * | 4/2021 | Calderoni | A61B 90/03 |
| 11,000,281 | B2 * | 5/2021 | Stamp | A61B 17/0682 |
| 11,020,112 | B2 * | 6/2021 | Shelton, IV | A61B 17/3417 |
| 11,350,939 | B2 * | 6/2022 | Sgroi, Jr | A61B 17/1155 |
| 11,627,959 | B2 * | 4/2023 | Shelton, IV | A61B 17/2833 227/175.1 |
| 11,690,624 | B2 * | 7/2023 | Eisinger | A61B 17/105 227/180.1 |
| 11,819,209 | B2 * | 11/2023 | Prema Mohanasundaram | A61B 17/07207 |
| 11,857,186 | B2 * | 1/2024 | Satti, III | A61B 17/1285 |
| 2006/0259054 | A1 | 11/2006 | Masuda et al. | |
| 2008/0172051 | A1 | 7/2008 | Masuda et al. | |
| 2009/0281554 | A1 * | 11/2009 | Viola | A61B 17/068 606/142 |
| 2010/0213240 | A1 * | 8/2010 | Kostrzewski | A61B 17/3209 227/180.1 |
| 2011/0006102 | A1 * | 1/2011 | Kostrzewski | A61B 17/1155 227/176.1 |
| 2012/0116391 | A1 * | 5/2012 | Houser | A61B 34/76 606/1 |
| 2012/0234895 | A1 * | 9/2012 | O'Connor | A61B 90/06 227/176.1 |
| 2014/0110456 | A1 * | 4/2014 | Taylor | A61B 90/90 227/176.1 |
| 2014/0263541 | A1 * | 9/2014 | Leimbach | A61B 17/32 227/175.2 |
| 2014/0324015 | A1 | 10/2014 | Romoscanu | |
| 2015/0272560 | A1 | 10/2015 | Baldwin | |
| 2015/0272575 | A1 * | 10/2015 | Leimbach | A61B 90/96 227/175.3 |
| 2016/0051259 | A1 * | 2/2016 | Hopkins | A61B 17/07207 |
| 2016/0106418 | A1 * | 4/2016 | Shi | A61B 17/068 227/175.2 |
| 2016/0120586 | A1 | 5/2016 | Spycher et al. | |
| 2016/0192934 | A1 * | 7/2016 | Williams | A61B 17/1155 29/451 |
| 2016/0361057 | A1 * | 12/2016 | Williams | A61B 17/068 |
| 2017/0281187 | A1 * | 10/2017 | Shelton, IV | A61B 17/072 |
| 2017/0281189 | A1 * | 10/2017 | Nalagatla | A61B 17/115 |
| 2018/0168633 | A1 * | 6/2018 | Shelton, IV | A61B 17/07207 |
| 2018/0235620 | A1 * | 8/2018 | Shelton, IV | A61B 17/07207 |
| 2018/0296213 | A1 * | 10/2018 | Strobl | A61B 18/1445 |
| 2018/0333169 | A1 * | 11/2018 | Leimbach | H02J 5/00 |
| 2018/0368847 | A1 * | 12/2018 | Shelton, IV | A61B 17/07207 |
| 2019/0083818 | A1 * | 3/2019 | Mitchell | A61B 17/225 |
| 2019/0183504 | A1 * | 6/2019 | Shelton, IV | A61B 17/07207 |
| 2020/0405292 | A1 * | 12/2020 | Shelton, IV | H01M 10/488 |
| 2021/0153929 | A1 * | 5/2021 | Oshiro | A61B 17/32 |
| 2023/0051981 | A1 * | 2/2023 | Asahina | A61B 17/320092 |
| 2023/0073915 | A1 * | 3/2023 | Inui | B06B 1/0611 |

FOREIGN PATENT DOCUMENTS

| | | | |
|---|---|---|---|
| JP | 2018099529 A | 6/2018 | |
| JP | 6495274 B2 * | 4/2019 | A61B 17/11 |
| WO | WO-2005122918 A1 | 12/2005 | |

* cited by examiner

TREATMENT INSTRUMENT

CROSS-REFERENCE TO RELATED APPLICATION

This application is a continuation of International Application No. PCT/JP2020/021673, filed on Jun. 1, 2020, the entire contents of which are incorporated herein by reference.

BACKGROUND

1. Technical Field

The present disclosure relates to a treatment tool.

2. Related Art

In the related art, a treatment tool applies energy to a site to be treated in living tissue (hereinafter, referred to as a target site) to treat the target site (see, for example, Japanese Patent Application Laid-open No. 2014-236984).

A treatment tool described in Japanese Patent Application Laid-open No. 2014-236984 includes a jaw that is openable and closable, an elongated inner pipe having a distal end portion connected to the jaw, a movable tubular portion connected to a proximal end portion of the inner pipe, and a movable handle that receives operation by an operator. The jaw is opened or closed by movement of the movable tubular portion and inner pipe along a longitudinal axis according to operation on the movable handle.

The inner pipe of the treatment tool described in Japanese Patent Application Laid-open No. 2014-236984 is connected to the movable tubular portion as follows.

Firstly, an operator fixes a connection member to the proximal end portion of the inner pipe by welding. Thereafter, the operator inserts the proximal end portion into the movable tubular portion, inserts a connection pin into the movable tubular portion from an outer peripheral surface of the movable tubular portion, and fixes the connection pin to the connection member. The inner pipe is thereby connected to the movable tubular portion.

SUMMARY

In some embodiments, a treatment tool includes: an end effector configured to implement treatment of living tissue; an operation input portion configured to receive operation by an operator; a tubular portion provided along a longitudinal axis of the treatment tool, the tubular portion having a first end and a second end, the first end being connected to the end effector, the second end being provided with a first engagement portion; a driver configured to move along the longitudinal axis according to the operation on the operation input portion, the driver including a second engagement portion configured to engage with the first engagement portion; and a pusher configured to connect the tubular portion and the driver to each other by coming into contact with the tubular portion toward a central axis of the tubular portion in a state where the first engagement portion and the second engagement portion have engaged with each other.

In some embodiments, a treatment tool includes: an end effector configured to implement treatment of living tissue; an operation input portion configured to receive operation by an operator; a tubular portion provided along a longitudinal axis of the treatment tool, the tubular portion having a first end and a second end, the first end being connected to the end effector, the second end being provided with a first engagement portion; a driver configured to move along the longitudinal axis according to the operation on the operation input portion, the driver including a second engagement portion configured to engage with the first engagement portion; and a pusher configured to connect the tubular portion and the driver to each other by coming into contact with the tubular portion toward a central axis of the tubular portion in a state where the first engagement portion and the second engagement portion have engaged with each other, the pusher including at least one of an attachment maintaining portion and a thin portion, the attachment maintaining portion being configured to restrict movement of the pusher in a first direction opposite to an attachment direction in which the pusher is attached to the driver, the thin portion being thinner than part of the pusher, the part being other than the thin portion.

In some embodiments, a treatment tool includes: an end effector configured to implement treatment of living tissue; an operation input portion configured to receive operation by an operator; a tubular portion provided along a longitudinal axis of the treatment tool, the tubular portion having a first end and a second end, the first end being connected to the end effector, the second end being provided with a first engagement portion; a driver configured to move along the longitudinal axis according to the operation on the operation input portion, the driver including a second engagement portion configured to engage with the first engagement portion; and a pusher configured to connect the tubular portion and the driver to each other by coming into contact with the tubular portion toward a central axis of the tubular portion in a state where the first engagement portion and the second engagement portion have engaged with each other; and a fixing portion configured to fix the pusher to the driver.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes for implementing the disclosure (hereinafter, embodiments) will be described hereinafter while reference is made to the drawings. The disclosure is not limited by the embodiments described hereinafter. Furthermore, any portions that are the same will be assigned with the same reference sign, throughout the drawings.

Schematic Configuration of Treatment System

Figure 1:
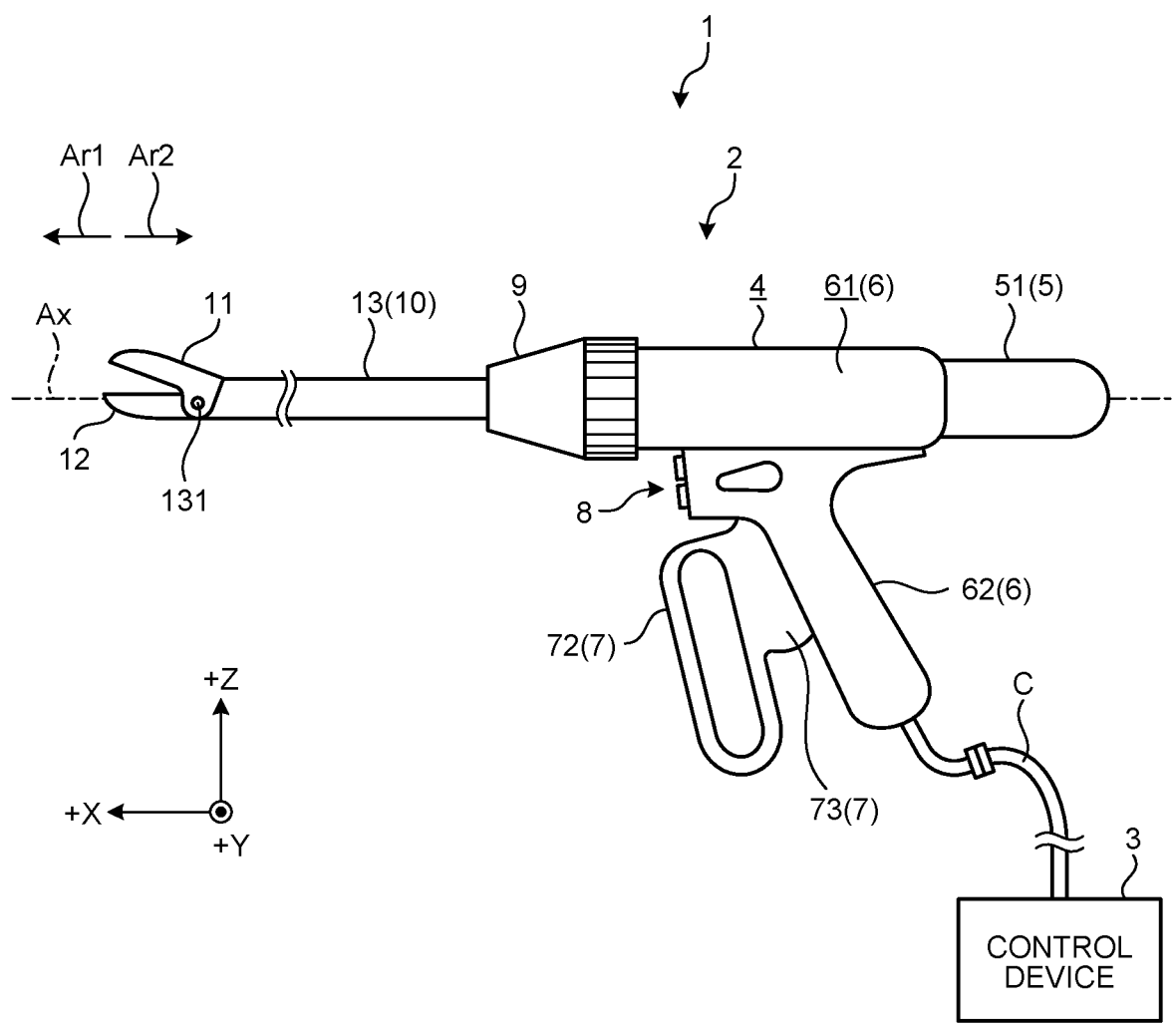
FIG. 1 is a diagram illustrating a treatment system according to a first embodiment.

FIG. 1 is a diagram illustrating a treatment system 1 according to a first embodiment.

The treatment system 1 is for applying ultrasound energy and high frequency energy to a site to be treated in living tissue (hereinafter, referred to as a target site) to treat the target site. Treatment that is able to be executed by the treatment system 1 according to the first embodiment is, for example, coagulation (sealing) of a target site, or incision of a target site. Furthermore, the treatment may also be treatment in which the coagulation and the incision are performed at the same time. The treatment system 1 includes, as illustrated in FIG. 1, a treatment tool 2 and a control device 3.

Configuration of Treatment Tool

In explanation of a configuration of the treatment tool 2, X, Y, and Z coordinate axes that are an X-axis, a Y-axis, and a Z-axis, which are orthogonal to one another, will be used hereinafter. The X-axis is an axis parallel to a central axis Ax (FIG. 1) of a sheath 10. The central axis Ax corresponds to a longitudinal axis. The Y-axis is an axis orthogonal to the plane of paper of FIG. 1. The Z-axis is an axis along a vertical direction in FIG. 1. Furthermore, one direction along the central axis Ax (in a positive direction along the X-axis) will hereinafter be referred to as a distal direction Ar1 and the other direction along the central axis Ax (in a negative direction along the X-axis) will hereinafter be referred to as a proximal direction Ar2.

Figure 2:
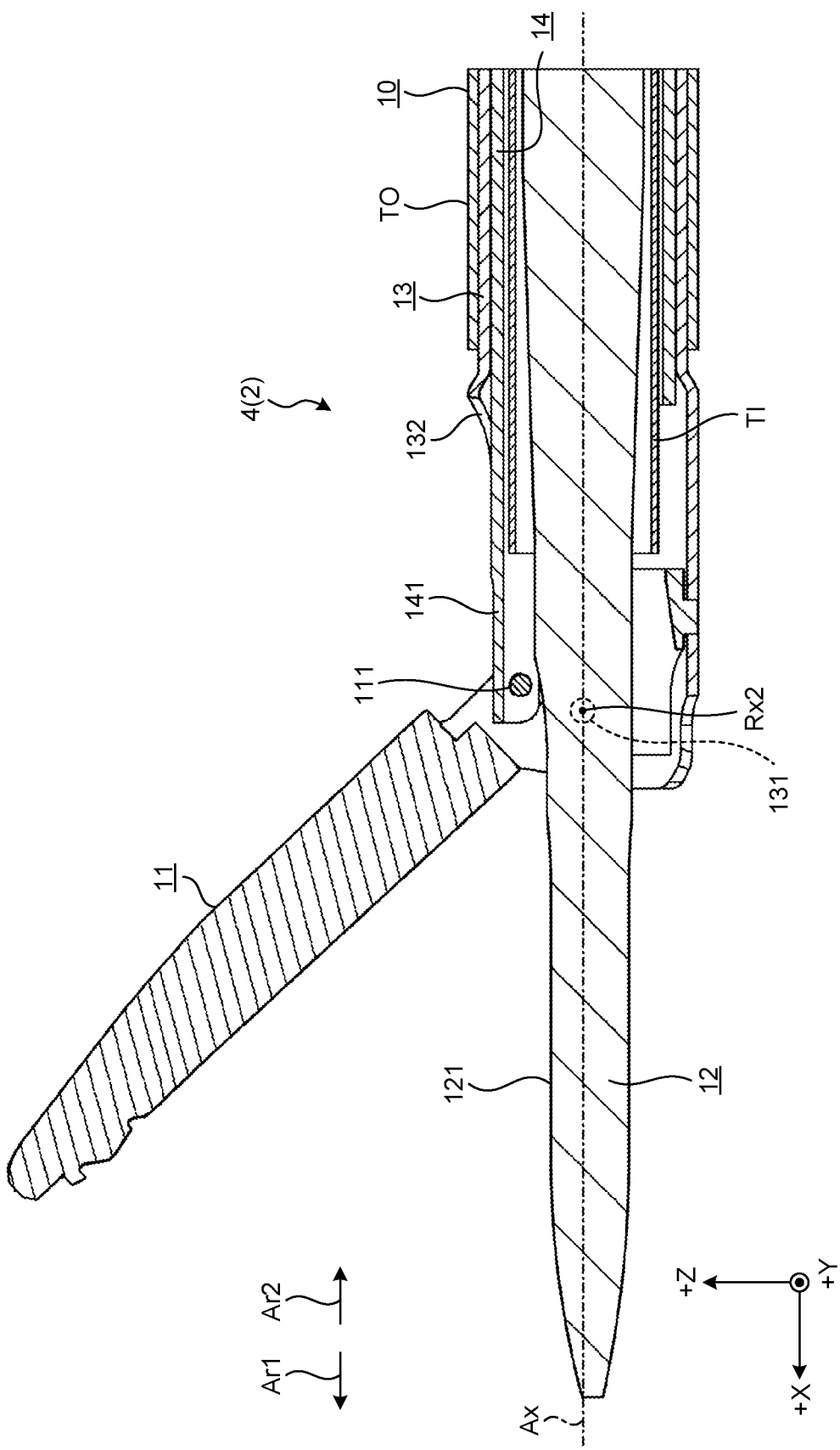
FIG. 2 is a diagram illustrating a configuration of a treatment tool.
Figure 3:
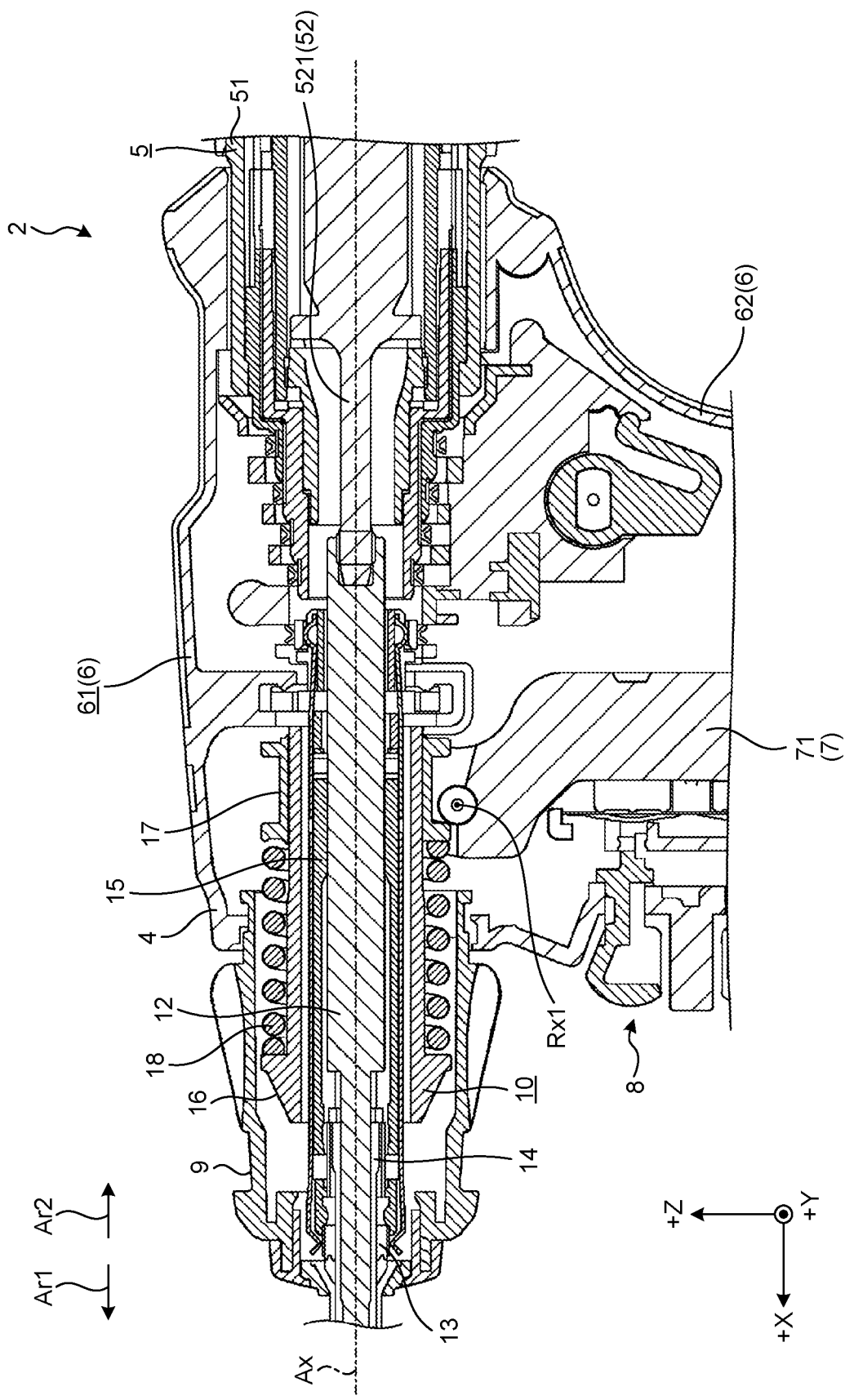
FIG. 3 is a diagram illustrating a configuration of the treatment tool.

FIG. 2 and FIG. 3 are diagrams illustrating the configuration of the treatment tool 2. Specifically, FIG. 2 and FIG. 3 are sectional diagrams of the treatment tool 2 cut along an X-Z plane including the central axis Ax and viewed from a positive direction along the Y-axis.

The treatment tool 2 is an ultrasound treatment tool for treatment of a target site by application of ultrasound energy and high frequency energy to the target site. This treatment tool 2 includes, as illustrated in FIG. 1 to FIG. 3, a handpiece 4 and an ultrasound transducer unit 5 (FIG. 1 and FIG. 3).

The handpiece 4 includes, as illustrated in FIG. 1 to FIG. 3, a holding case 6 (FIG. 1 and FIG. 3), a movable handle 7 (FIG. 1 and FIG. 3), a switch 8 (FIG. 1 and FIG. 3), a rotation knob 9 (FIG. 1 and FIG. 3), the sheath 10, a jaw 11 (FIG. 1 and FIG. 2), and a vibration transmission portion 12.

The holding case 6 supports the whole treatment tool 2. This holding case 6 includes, as illustrated in FIG. 1 or FIG. 3, a holding case body 61 that is coaxial with the central axis Ax and approximately cylindrical, and a fixed handle 62 that extends in the negative direction along the Z-axis from the holding case body 61 and is grasped by an operator, such as an operating surgeon.

The movable handle 7 corresponds to an operation input portion. The movable handle 7 receives each of a closing operation and an opening operation by an operator, such as an operating surgeon. This movable handle 7 includes, as illustrated in FIG. 1 or FIG. 3, a handle base portion 71 (FIG. 3), an operating portion 72 (FIG. 1), and a connection portion 73 (FIG. 1).

The handle base portion 71 is positioned inside the holding case 6. A portion of the handle base portion 71, the portion being in a positive direction along the Z-axis, is rotatably supported about a first rotation axis Rx1 (FIG. 3) parallel to the Y-axis, by the holding case 6. Furthermore, an end portion of the handle base portion 71, the end portion being in the positive direction along the Z-axis, protrudes in the positive direction along the Z-axis in a biforked state and is engaged with a slider 17 of the sheath 10.

The operating portion 72 is a portion that receives each of the closing operation and the opening operation by an operator, such as an operating surgeon, and is positioned outside the holding case 6, as illustrated in FIG. 1.

The connection portion 73 is a portion that is provided to extend inside and outside the holding case 6 and connects the handle base portion 71 and the operating portion 72 to each other.

The movable handle 7 rotates anticlockwise in FIG. 3 about the first rotation axis Rx1 in a case where the movable handle 7 receives the closing operation by an operator, such as an operating surgeon. That is, the operating portion 72 moves in a direction approaching the fixed handle 62. By contrast, the movable handle 7 rotates clockwise in FIG. 3 about the first rotation axis Rx1 in a case where the opening operation on the movable handle 7 is received. That is, the operating portion 72 moves in a direction separating from the fixed handle 62.

The switch 8 is provided, as illustrated in FIG. 1 or FIG. 3, in a state of being exposed outside from a side surface of the fixed handle 62, the side surface being in the distal direction Ar1. The switch 8 receives treatment operation by an operator, such as an operating surgeon. The treatment operation is operation for application of ultrasound energy or high frequency energy to a target site.

The rotation knob 9 has an approximately cylindrical shape coaxial with the central axis Ax and is provided, as illustrated in FIG. 3, near an end of the holding case body 61, the end being in the distal direction Ar1. The rotation knob 9 receives rotating operation by an operator, such as an operating surgeon. The rotating operation rotates the rotation knob 9 about the central axis Ax, relatively to the holding case body 61. Furthermore, the rotation of the rotation knob 9 rotates the jaw 11 and the vibration transmission portion 12 about the central axis Ax.

The sheath 10 has an approximately cylindrical shape overall. The sheath 10 includes, as illustrated in FIG. 1 to FIG. 3, an outer pipe 13, an inner pipe 14 (FIG. 2 and FIG. 3), a holding portion 15 (FIG. 3), a slider receiver 16 (FIG. 3), and the slider 17 (FIG. 3).

The outer pipe 13 is a cylindrical pipe formed of a material, such as metal.

An outer peripheral surface of this outer pipe 13 is covered with an outer tube TO (FIG. 2) that is electrically insulating.

Furthermore, a first pin 131 (FIG. 1 and FIG. 2) is fixed to an end portion of the outer pipe 13, the end portion being in the distal direction Ar1, the first pin 131 extending in a direction orthogonal to the plane of paper of FIG. 1 and FIG. 2 and supporting the jaw 11 rotatably about a second rotation axis Rx2.

Furthermore, in the positive direction along the Z-axis, a notched portion 132 (FIG. 2) is formed in the end portion of the outer pipe 13, the end portion being in the distal direction Ar1, the notched portion 132 extending from a distal end of the outer pipe 13 in the proximal direction Ar2.

The inner pipe 14 corresponds to a tubular portion. The inner pipe 14 is a cylindrical pipe having a diameter with a dimension smaller than that of the outer pipe 13. Furthermore, the inner pipe 14 is inserted in the outer pipe 13 in a state of being coaxial with the outer pipe 13.

An arm portion 141 that protrudes in the distal direction Ar1 is provided, as illustrated in FIG. 2, in the inner pipe 14, the arm portion 141 being in the positive direction along the Z-axis at an end portion of the inner pipe 14, the end portion being in the distal direction Ar1. A second pin 111 provided in the jaw 11 and extending parallel to the second rotation axis Rx2 (the first pin 131) is inserted in this arm portion 141.

The holding portion 15 is formed of a material that is electrically insulating, such as resin, and has an approximately cylindrical shape. This holding portion 15 is inserted in the rotation knob 9 and the holding case body 61, in a state of extending over the rotation knob 9 and the holding case body 61, as illustrated in FIG. 3. The holding portion 15 holds the vibration transmission portion 12 that has been inserted in the holding portion 15. Furthermore, the holding portion 15 is mechanically connected to the rotation knob 9 and the outer pipe 13 at an end portion of the holding portion 15, the end portion being in the distal direction Ar1. That is, the holding portion 15, the outer pipe 13, the jaw 11, and the vibration transmission portion 12 rotate, together with the rotation knob 9, about the central axis Ax, according to the rotating operation on the rotation knob 9 by an operator, such as an operating surgeon.

The slider receiver 16 corresponds to a driver. The slider receiver 16 is formed of a material that is electrically insulating, such as resin, and has an approximately cylindrical shape. The slider receiver 16 is provided movably along the central axis Ax relatively to the holding portion 15, in a state where the holding portion 15 has been inserted in the slider receiver 16. An end portion of the slider receiver 16, the end portion being in the distal direction Ar1, is connected to an end portion of the inner pipe 14, the end portion being in the proximal direction Ar2, in a state where the end portion of the slider receiver 16 is allowed to move along the central axis Ax relatively to the holding portion 15 but restricted from rotating about the central axis Ax. That is, the slider receiver 16 and the inner pipe 14 rotate, together with the rotation knob 9, about the central axis Ax, according to the rotating operation on the rotation knob 9 by an operator, such as an operating surgeon.

A connection structure between the inner pipe 14 and the slider receiver 16 will be described later.

The slider 17 has an approximately cylindrical shape and is provided movably along the central axis Ax, relatively to the slider receiver 16, in a state where the slider receiver 16 has been inserted in the slider 17. The slider 17 is engaged with the movable handle 7 (the end portion of the handle base portion 71, the end portion being in the positive direction along the Z-axis) as described above.

The slider 17, the slider receiver 16, and the inner pipe 14 operate as described below, according to operations on the movable handle 7 by an operator, such as an operating surgeon.

In response to a closing operation on the movable handle 7 by an operator, such as an operating surgeon, the slider 17 is pushed in the distal direction Ar1 along the central axis Ax by the movable handle 7 (the end portion of the handle base portion 71, the end portion being in the positive direction along the Z-axis). Furthermore, the slider receiver 16 receives pressing force in the distal direction Ar1 from the slider 17 via a coil spring 18 (FIG. 3) provided between the slider receiver 16 and the slider 17. The inner pipe 14 moves, in association with the slider receiver 16, in the distal direction Ar1 along the central axis Ax. The arm portion 141 pushes the second pin 111 in the distal direction Ar1. The jaw 11 then rotates anticlockwise in FIG. 2 about the second rotation axis Rx2. In this rotation, because the second pin 111 also moves, in a state of maintaining a certain distance, about the second rotation axis Rx2, the arm portion 141 moves in the distal direction Ar1 while being deformed in the positive direction along the Z-axis where the notched portion 132 is provided. That is, the jaw 11 moves in a direction (a closing direction) approaching an end portion 121 (FIG. 2) of the vibration transmission portion 12, the end portion 121 being in the distal direction Ar1.

Furthermore, according to the opening operation on the movable handle 7 by an operator, such as an operating surgeon, the jaw 11 rotates clockwise in FIG. 2 about the second rotation axis Rx2. That is, the jaw 11 moves in a direction (an opening direction) separating from the end portion 121 of the vibration transmission portion 12, the end portion 121 being in the distal direction Ar1.

As described above, the jaw 11 opens and closes relatively to the end portion 121 of the vibration transmission portion 12 according to operation on the movable handle 7 by an operator, such as an operating surgeon, the end portion 121 being in the distal direction Ar1, and grips a target site between the jaw 11 and the end portion 121. The jaw 11 and the end portion 121 correspond to an end effector.

The coil spring 18 mentioned above transmits drive force according to operation on the movable handle 7 by an operator, such as an operating surgeon, to the slider receiver 16, and corresponds to an elastic material. The coil spring 18 is used to maintain grip force for gripping a target site between the jaw 11 and the end portion 121 (FIG. 2) of the vibration transmission portion 12, the end portion 121 being in the distal direction Ar1.

At least part of the jaw 11 is formed of an electrically conducting material.

The vibration transmission portion 12 is formed of an electrically conducting material and has an elongated shape linearly extending along the central axis Ax. Furthermore, the vibration transmission portion 12 is inserted in the sheath 10 in a state where its end portion 121 in the distal direction Ar1 protrudes outside, as illustrated in FIG. 2. In this state, an end portion of the vibration transmission portion 12, the end portion being in the proximal direction Ar2, is mechanically connected to the ultrasound transducer unit 5, as illustrated in FIG. 3. That is, the vibration transmission portion 12 transmits ultrasound vibration generated by the ultrasound transducer unit 5, to its end portion 121 in the distal direction Ar1 from its end portion in the proximal direction Ar2. In this first embodiment, the ultrasound vibration is longitudinal vibration that is vibration along the central axis Ax.

An outer peripheral surface of the vibration transmission portion 12 is covered with an inner tube TI (FIG. 2) that is electrically insulating, to provide electric insulation between: the outer pipe 13 and the inner pipe 14; and the vibration transmission portion 12.

The ultrasound transducer unit 5 includes, as illustrated in FIG. 1 or FIG. 3, a transducer (TD) case 51 and an ultrasound transducer 52 (FIG. 3).

The TD case 51 supports the ultrasound transducer 52 and is detachably connected to the holding case body 61.

The ultrasound transducer 52 generates ultrasound vibration, under control by the control device 3. In this first embodiment, the ultrasound transducer 52 is a bolt-clamped Langevin transducer (BLT). For convenience of explanation, FIG. 3 illustrates only a front mass 521 of the ultrasound transducer 52 (BLT), the front mass 521 being connected to the end portion of the vibration transmission portion 12, the end portion being in the proximal direction Ar2.

Configuration of Control Device

The control device 3 integrally controls operation of the treatment tool 2 through an electric cable C (FIG. 1).

Specifically, the control device 3 detects the treatment operation on the switch 8 by an operator, such as an operating surgeon, through the electric cable C. In a case where the control device 3 has detected the treatment operation, the control device 3 applies ultrasound energy or high frequency energy to a target site gripped between the jaw 11 and the end portion 121 of the vibration transmission portion 12, the end portion 121 being in the distal direction Ar1, via the electric cable C. That is, the control device 3 performs treatment of the target site.

For example, in applying ultrasound energy to a target site, the control device 3 supplies drive power to the ultrasound transducer 52 through the electric cable C. The ultrasound transducer 52 thereby generates longitudinal vibration (ultrasound vibration) that is vibration along the central axis Ax. Furthermore, the longitudinal vibration causes the end portion 121 of the vibration transmission portion 12 to vibrate at desired amplitude, the end portion 121 being in the distal direction Ar1. From the end portion 121, ultrasound vibration is applied to the target site gripped between the jaw 11 and the end portion 121. In other words, ultrasound energy is applied to the target site from the end portion 121.

Furthermore, for example, in applying high frequency energy to a target site, the control device 3 supplies high frequency power between the jaw 11 and the vibration transmission portion 12 through the electric cable C. High frequency electric current thereby flows in the target site gripped between the jaw 11 and the end portion 121 of the vibration transmission portion 12, the end portion 121 being in the distal direction Ar1. In other words, high frequency energy is applied to the target site.

Connection Structure between Inner Pipe and Slider Receiver

The connection structure between the inner pipe 14 and the slider receiver 16 will be described next.

Figure 4:
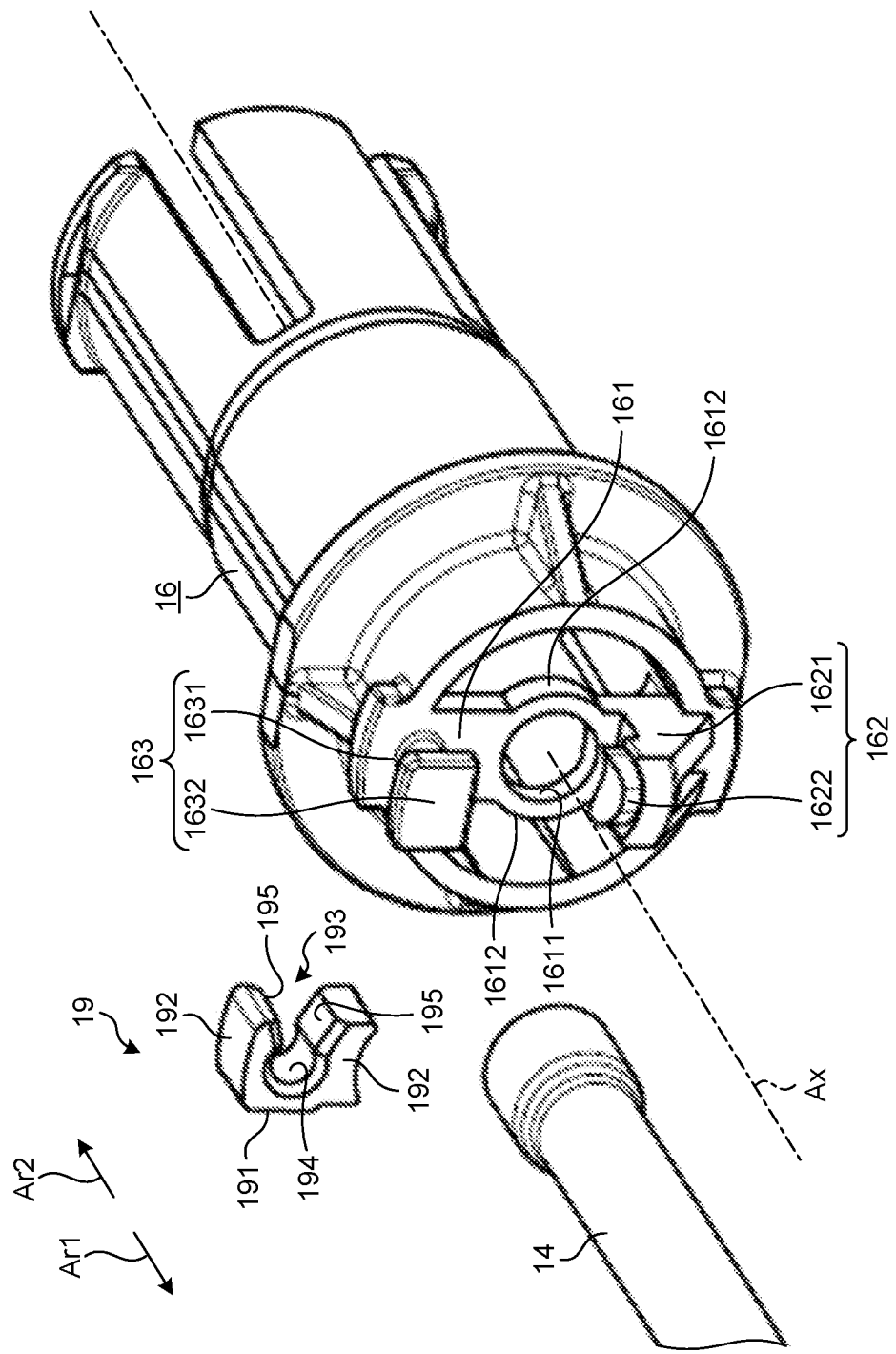
FIG. 4 is a diagram illustrating a connection structure between an inner pipe and a slider receiver.
Figure 5:
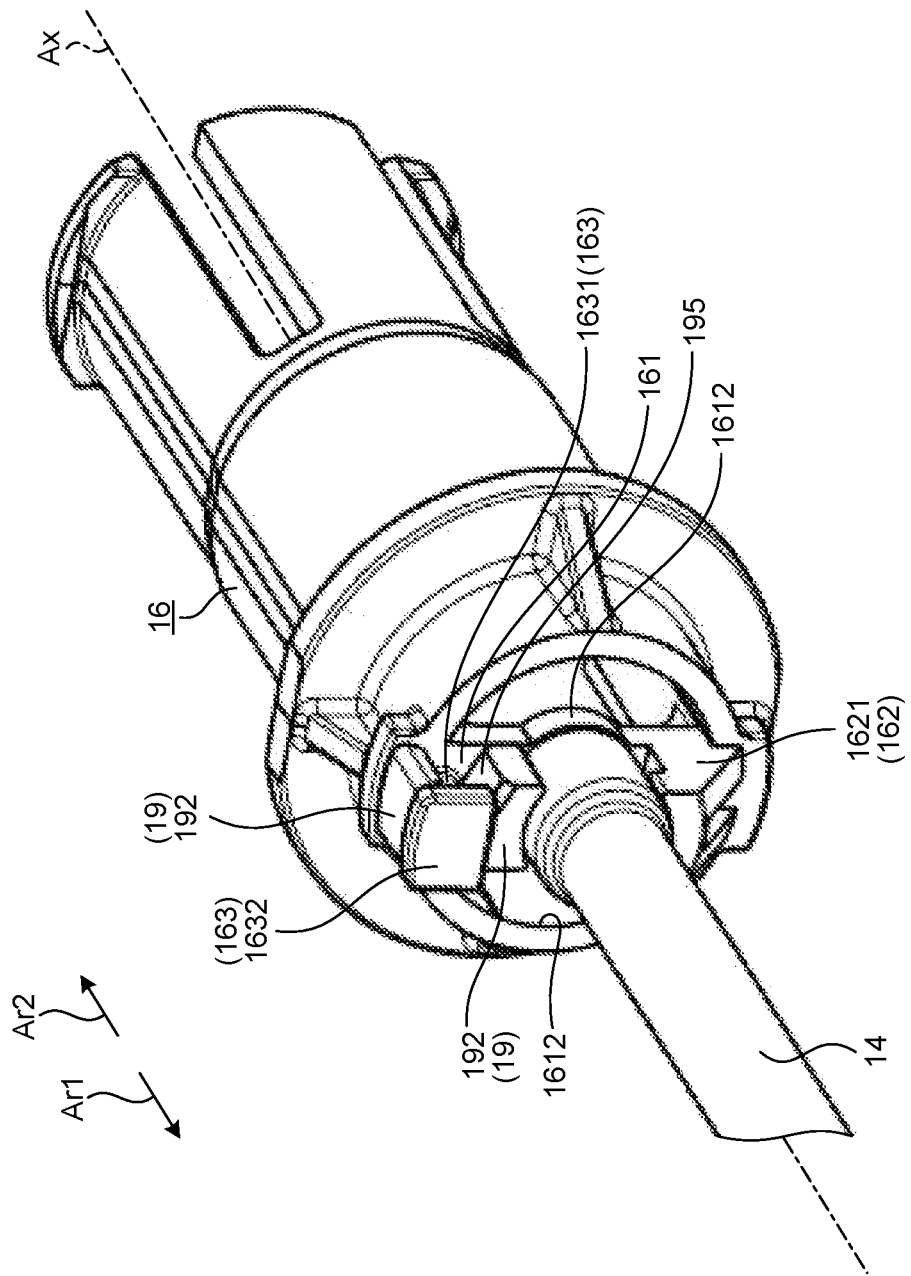
FIG. 5 is a diagram illustrating the connection structure between the inner pipe and the slider receiver.
Figure 6:
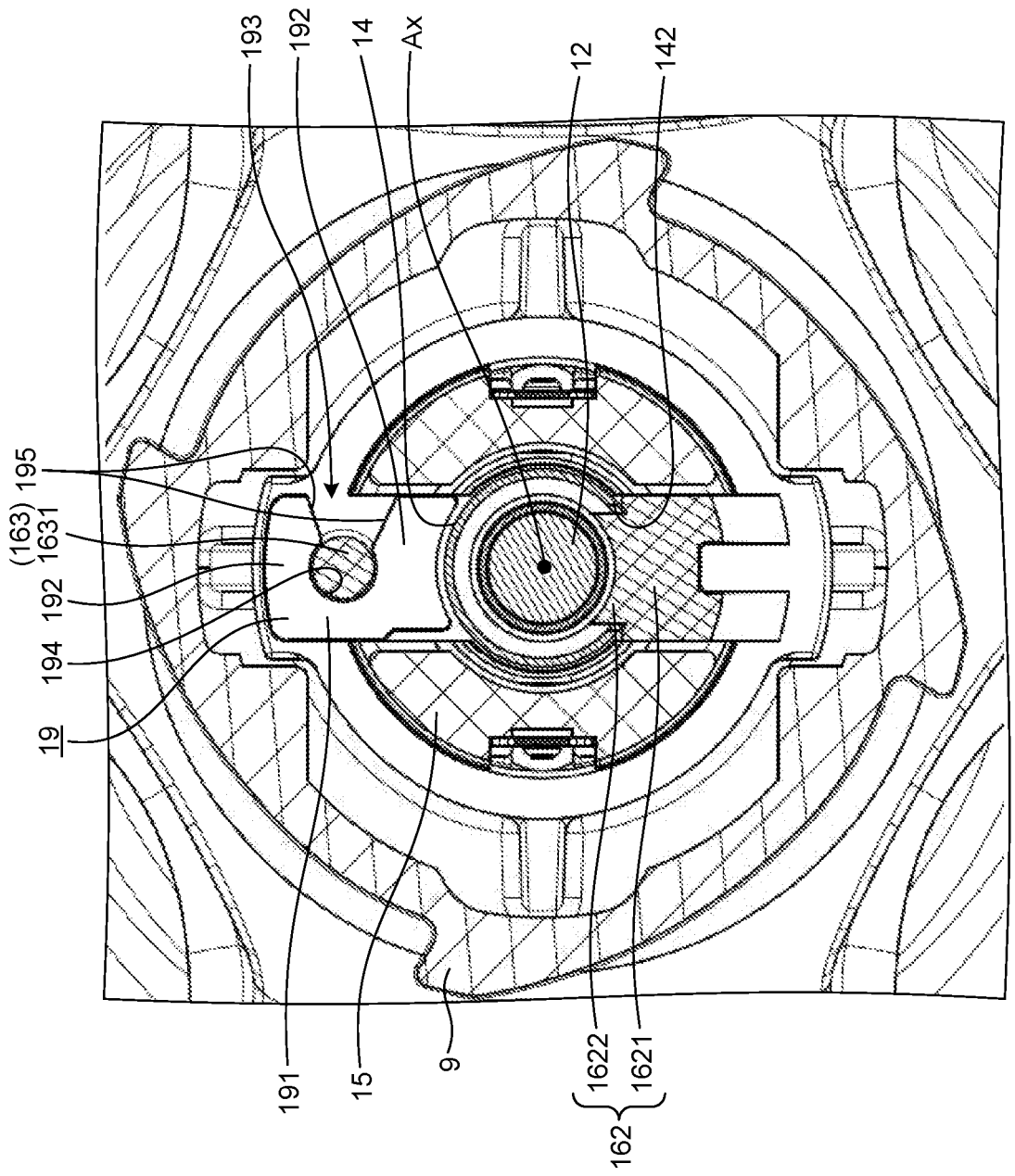
FIG. 6 is a diagram illustrating the connection structure between the inner pipe and the slider receiver.
Figure 7:
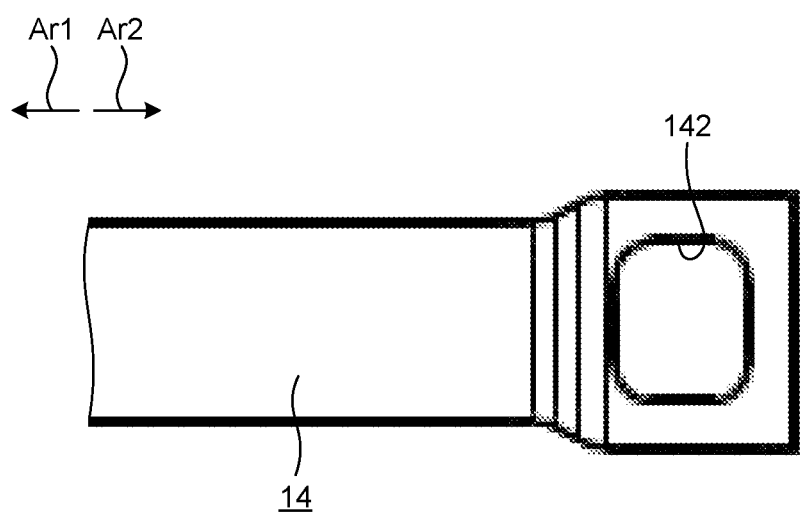
FIG. 7 is a diagram illustrating the connection structure between the inner pipe and the slider receiver.

FIG. 4 to FIG. 7 are diagrams illustrating the connection structure between the inner pipe 14 and the slider receiver 16. Specifically, FIG. 4 is an exploded perspective view of a connection between the end portion of the inner pipe 14, the end portion being in the proximal direction Ar2, and the slider receiver 16. FIG. 5 is a perspective view of a state where the end portion of the inner pipe 14, the end portion being in the proximal direction Ar2, and the slider receiver 16 have been connected to each other. FIG. 6 is a sectional diagram of the connection between the end portion of the inner pipe 14, the end portion being in the proximal direction Ar2, and the slider receiver 16, the connection being cut along a plane orthogonal to the central axis A. FIG. 7 is a diagram illustrating a first engagement portion 142 provided at the end portion of the inner pipe 14, the end portion being in the proximal direction Ar2.

The first engagement portion 142 that engages with the slider receiver 16 is provided at the end portion of the inner pipe 14, the end portion being in the proximal direction Ar2, as illustrated in FIG. 7. In this embodiment, the first engagement portion 142 is a notch (through hole) penetrating an outer peripheral surface and an inner peripheral surface of the inner pipe 14, the notch being approximately rectangular.

A connection base body 161, a first connection portion 162, and a second connection portion 163 are provided at the end portion of the slider receiver 16, the end portion being in the distal direction Ar1, as illustrated in FIG. 4 to FIG. 6.

The connection base body 161 is a portion where the first and second connection portions 162 and 163 are provided. As illustrated in FIG. 4, this connection base body 161 has a flat plate shape, has a plate surface orthogonal to the central axis Ax, and bridges between portions of an inner peripheral surface of the slider receiver 16 in a posture where the connection base body 161 strides over the central axis Ax.

An insertion hole 1611 penetrating both sides of the connection base body 161, having the central axis Ax at the center of the insertion hole 1611, and being circular is provided at the position of the central axis Ax in the connection base body 161, as illustrated in FIG. 4. This insertion hole 1611 is a hole where the vibration transmission portion 12 is inserted in.

Furthermore, each of a pair of holes 1612 provided between the inner peripheral surface of the slider receiver 16 and the connection base body 161 functions as a hole where the holding portion 15 is inserted in.

The first connection portion 162 is a portion connected to the end portion of the inner pipe 14, the end portion being in the proximal direction Ar2. The first connection portion 162 includes, as illustrated in FIG. 4 to FIG. 6, a base 1621 and a second engagement portion 1622 (FIG. 4 and FIG. 6).

The base 1621 is a portion protruding in the distal direction Ar1 from a position on a plate surface of the connection base body 161, the plate surface being in the distal direction Ar1, the position being below the insertion hole 1611 in FIG. 4.

The second engagement portion 1622 is a projection provided on an upper surface of the base 1621 and protruding upward, in FIG. 4 and FIG. 6. A tip (an upper end surface in FIG. 4 and FIG. 6) of the second engagement portion 1622 is formed of an arc-shaped concave curved surface having the central axis Ax at the center of the arc, to avoid the vibration transmission portion 12 inserted in the insertion hole 1611. The second engagement portion 1622 has an outer shape slightly smaller than the inner shape of the first engagement portion 142, and engages with the first engagement portion 142 by being fitted in the first engagement portion 142.

The second connection portion 163 is a portion where a pusher 19 described later is connected to. This second connection portion 163 includes, as illustrated in FIG. 4 to FIG. 6, a protruding portion 1631 and a retaining portion 1632 (FIG. 4 and FIG. 5).

The protruding portion 1631 is a portion where the pusher 19 is attached to. This protruding portion 1631 has a columnar shape protruding in the distal direction Ar1 from a position on the plate surface of the connection base body 161, the plate surface being in the distal direction Ar1, the position being above the insertion hole 1611 in FIG. 4.

The retaining portion 1632 is a portion that is provided on a tip (an end surface in the distal direction Ar1) of the protruding portion 1631 and that prevents the pusher 19 from falling off the tip of the protruding portion 1631, the pusher 19 having been attached to the protruding portion 1631.

The pusher 19 is a member that maintains a state where the second engagement portion 1622 has been fitted in the first engagement portion 142, in other words, a state where the end portion of the inner pipe 14 has been connected to the slider receiver 16, the end portion being in the proximal direction Ar2. This pusher 19 includes, as illustrated in FIG. 4 to FIG. 6, a base portion 191 (FIG. 4 and FIG. 6) and a pair of protruding portions 192.

The base portion 191 is a portion extending vertically in FIG. 4 and FIG. 6.

The pair of protruding portions 192 are portions respectively protruding from upper and lower end portions of the base portion 191 in FIG. 4 and FIG. 6, to be approximately parallel to each other. That is, the pusher 19 is approximately U-shaped overall. Furthermore, an opening in the U-shape of the pusher 19 corresponds to an opening 193.

A fitting recessed portion 194 and a pair of inclined surfaces 195 are provided inside the U-shape of the pusher 19, as illustrated in FIG. 4 or FIG. 6.

The fitting recessed portion 194 is a portion where the protruding portion 1631 is fitted in, and is formed of an arc-shaped concave curved surface following an outer peripheral shape of the protruding portion 1631.

The pair of inclined surfaces 195 are inclined surfaces separating from each other toward the opening 193 from positions where the pair of inclined surfaces 195 are respectively in contact with the fitting recessed portion 194.

A method of connecting the inner pipe 14 and the slider receiver 16 to each other will be described next.

Firstly, an operator fits the second engagement portion 1622 in the first engagement portion 142 while placing a proximal end of the inner pipe 14 over the plate surface of the connection base body 161, the plate surface being in the distal direction Ar1.

Subsequently, the operator holds the pusher 19 in the operator's hand, and places the protruding portion 1631 inside the U-shape of the pusher 19 from the opening 193. In this placement, tips of the pair of protruding portions 192 of the pusher 19 are elastically deformed in directions separating from each other with the base portion 191 being a base point, by the protruding portion 1631 sliding on the pair of inclined surfaces 195 and the pair of protruding portions 192 being pressed by the protruding portion 1631. The pusher 19 returns to the original shape, by the protruding portion 1631 being fitted in the fitting recessed portion 194. The pusher 19 is thereby attached to the protruding portion 1631. In this state, the pusher 19 is provided at a position across the inner pipe 14 from the second engagement portion 1622. By pressing the outer peripheral surface of the inner pipe 14 toward the central axis Ax, the pusher 19 maintains the state where the second engagement portion 1622 has been fitted in the first engagement portion 142. That is, the inner pipe 14 is fixed to the slider receiver 16.

An operator is able to detach the inner pipe 14 from the slider receiver 16 by performing operation opposite to that in the above described connection method.

The above described first embodiment has the following effects.

The inner pipe 14 and the slider receiver 16 in the treatment tool 2 according to the first embodiment are able to be fixed to each other just by fitting of the second engagement portion 1622 in the first engagement portion 142 and attachment of the pusher 19 to the protruding portion 1631.

Therefore, in fixing the inner pipe 14 to the slider receiver 16, welding is no longer required as conventionally done and the ease of assembly is able to be improved.

The inner pipe 14 and the slider receiver 16 are structured to advance and retract along the central axis Ax. Therefore, large force along the central axis Ax is applied to the inner pipe 14 and the slider receiver 16.

Because the above described structure is adopted for attachment of the pusher 19 to the protruding portion 1631 in the treatment tool 2 according to the first embodiment, the large force mentioned above is not applied to the pusher 19. That is, the first embodiment enables: improvement in the ease of assembly; and implementation of a structure that enables transmission of drive force required for opening and closing of the jaw 11.

For the possibility of effective utilization of resources, reduction of medical waste, and reduction of medical spending, remanufacturing of treatment tools has attracted attention in recent years.

Remanufacturing of a treatment tool means disassembling a used treatment tool after treatment of a target site, cleaning the disassembled treatment tool, replacing some parts, reassembling the treatment tool, sterilizing the reassembled treatment tool, checking that the treatment tool has the performance required, and thereby enabling the treatment tool to be used again.

The pusher 19 in the treatment tool 2 according to the first embodiment is detachably attached to the slider receiver 16. This facilitates remanufacturing of the treatment tool 2.

The pusher 19 in the treatment tool 2 according to the first embodiment is provided at the position across the inner pipe 14 from the second engagement portion 1622. Therefore, the state where the second engagement portion 1622 has been fitted in the first engagement portion 142 is able to be maintained well by just the single pusher 19. Accordingly, the number of parts is able to be reduced.

Second Embodiment

A second embodiment will be described next.

In the following description, any component that is the same as that of the above described first embodiment will be assigned with the same reference sign, and detailed description thereof will be omitted or simplified.

The second embodiment is different from the above described first embodiment in that the pusher 19 and the protruding portion 1631 are shaped differently in the second embodiment.

For convenience of explanation, the pusher 19 according to the second embodiment will hereinafter be referred to as a pusher 19A. The protruding portion 1631 according to the second embodiment will be referred to as a protruding portion 1631A.

Figure 8:
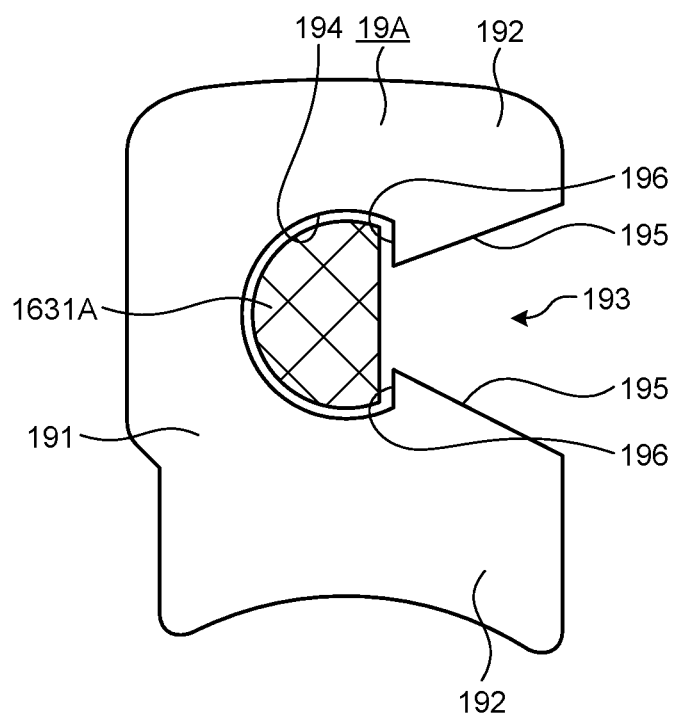
FIG. 8 is a diagram illustrating an attachment structure of a pusher according to a second embodiment.
Figure 8:
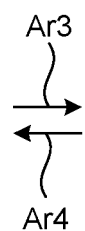

FIG. 8 is a diagram illustrating an attachment structure of the pusher 19A according to the second embodiment. Specifically, FIG. 8 is a sectional view corresponding to FIG. 6.

The pusher 19A according to the second embodiment is different from the pusher 19 according to the first embodiment in that a pair of attachment maintaining portions 196 are provided in the pusher 19A, as illustrated in FIG. 8.

The pair of attachment maintaining portions 196 are portions that restrict movement of the pusher 19A in an opposite direction Ar4 opposite to an attachment direction Ar3 (FIG. 8) in which the pusher 19A is attached to the protruding portion 1631A. Specifically, the pair of attachment maintaining portions 196 are respectively positioned at boundaries between the fitting recessed portion 194 and the pair of inclined surfaces 195, and respectively include planar portions extending in directions approaching each other and intersecting the opposite direction Ar4.

Furthermore, the protruding portion 1631A has a D-shaped cross section and has a surface that is planar correspondingly to the pair of attachment maintaining portions 196 described above, the surface being in the attachment direction Ar3.

That is, in this structure, the pair of attachment maintaining portions 196 restrict movement of the pusher 19A in the opposite direction Ar4 after the protruding portion 1631A has been fitted in the fitting recessed portion 194.

The second embodiment described above has effects similar to those of the above described first embodiment.

The second embodiment has the structure in which the pair of attachment maintaining portions 196 restrict movement of the pusher 19A in the opposite direction Ar4 after the protruding portion 1631A has been fitted in the fitting recessed portion 194. Therefore, the structure makes it difficult for a person to remanufacture the treatment tool, the person being unrelated to a manufacturer that remanufactures the treatment tool.

Third Embodiment

A third embodiment will be described next.

In the following description, any component that is the same as that of the above described first embodiment will be assigned with the same reference sign, and detailed description thereof will be omitted or simplified.

This third embodiment is different from the above described first embodiment in that the pusher 19 is differently shaped.

For convenience of explanation, the pusher 19 according to the third embodiment will hereinafter be referred to as a pusher 19B.

Figure 9:
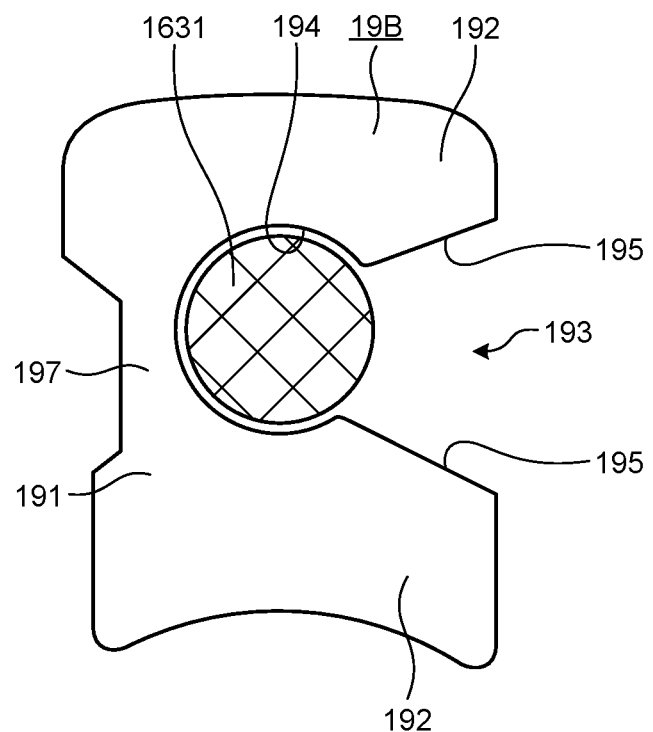
FIG. 9 is a diagram illustrating an attachment structure of a pusher according to a third embodiment.

FIG. 9 is a diagram illustrating an attachment structure of the pusher 19B according to the third embodiment. Specifically, FIG. 9 is a sectional view corresponding to FIG. 6.

The pusher 19B according to the third embodiment is different from the pusher 19 according to the first embodiment in that a thin portion 197 is provided in the pusher 19B, as illustrated in FIG. 9.

The thin portion 197 is a portion provided in part of the base portion 191, the part facing the opening 193 and being thinner than the other part of the base portion 191.

That is, the pusher 19B is structured so that in a case where detachment of the pusher 19B from the protruding portion 1631 is forcedly attempted after the protruding portion 1631 has been fitted in the fitting recessed portion 194, the pusher 19B is broken from the thin portion 197.

The third embodiment described above has effects similar to those of the above described first embodiment.

This third embodiment has the structure in which the pusher 19B is broken from the thin portion 197 in a case where detachment of the pusher 19B from the protruding portion 1631 is forcedly attempted after the protruding portion 1631 has been fitted in the fitting recessed portion 194. Therefore, the structure makes it difficult for a person to remanufacture the treatment tool, the person being unrelated to a manufacturer that remanufactures the treatment tool.

Fourth Embodiment

A fourth embodiment will be described next.

In the following description, any component that is the same as that of the above described first embodiment will be assigned with the same reference sign, and detailed description thereof will be omitted or simplified.

The fourth embodiment is different from the first embodiment described above in that a fixing portion 20C is additionally provided in the fourth embodiment.

Figure 10:
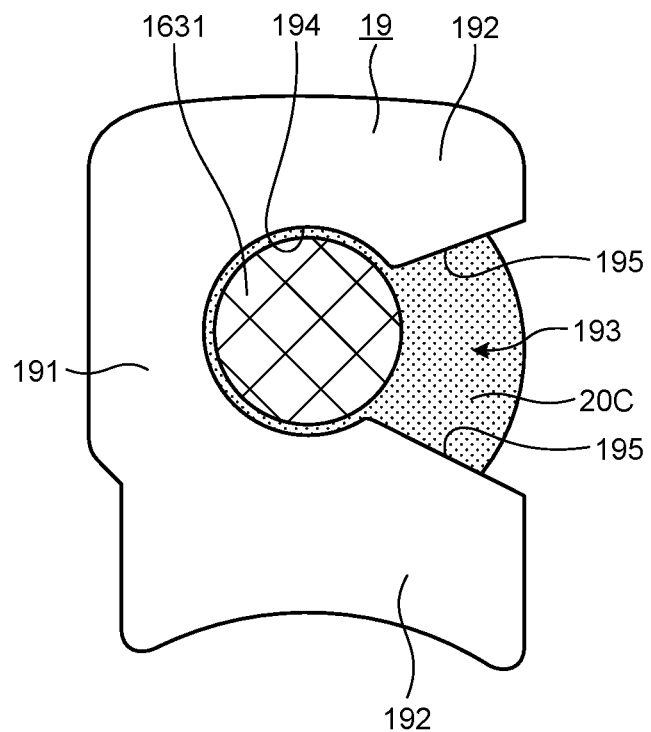
FIG. 10 is a diagram illustrating an attachment structure of a pusher according to a fourth embodiment.

FIG. 10 is a diagram illustrating an attachment structure of the pusher 19, according to the fourth embodiment. Specifically, FIG. 10 is a sectional view corresponding to FIG. 6.

The fixing portion 20C is a member that fixes the pusher 19 to the protruding portion 1631. In this fourth embodiment, the fixing portion 20C is an adhesive.

The fixing portion 20C is applied between the protruding portion 1631 and the pusher 19. That is, curing the fixing portion 20C achieves a structure disabling detachment of the pusher 19 from the protruding portion 1631.

The fourth embodiment described above has effects similar to those of the above described first embodiment.

The fourth embodiment has the structure in which the fixing portion 20C prevents the pusher 19 from being detached from the protruding portion 1631. Therefore, the structure enables prevention of remanufacturing of the treatment tool by a person being unrelated to a manufacturer that remanufactures the treatment tool.

Fifth Embodiment

A fifth embodiment will be described next.

In the following description, any component that is the same as that of the above described first embodiment will be assigned with the same reference sign, and detailed description thereof will be omitted or simplified.

The fifth embodiment is different from the first embodiment described above in that a fixing portion 20D is additionally provided in the fifth embodiment.

Figure 11:
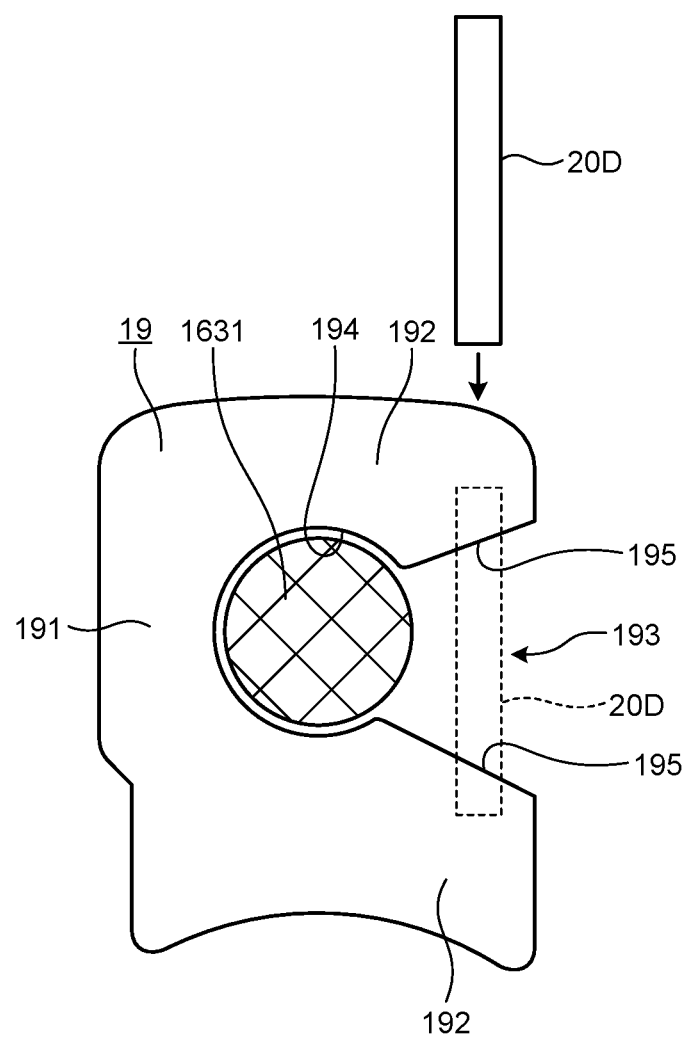
FIG. 11 is a diagram illustrating an attachment structure of a pusher according to a fifth embodiment.

FIG. 11 is a diagram illustrating an attachment structure of the pusher 19, according to the fifth embodiment. Specifically, FIG. 11 is a sectional view corresponding to FIG. 6.

The fixing portion 20D is a member that fixes the pusher 19 to the protruding portion 1631, similarly to the fixing portion 20C described above with respect to the third embodiment. In this fifth embodiment, the fixing portion 20D is a pin.

The fixing portion 20D is fixed to the pusher 19 in a posture where the fixing portion 20D bridges between the pair of inclined surfaces 195, after the pusher 19 has been attached to the protruding portion 1631. That is, this structure disables detachment of the pusher 19 from the protruding portion 1631 by the protruding portion 1631 getting caught on the fixing portion 20D.

The fifth embodiment described above has effects similar to those of the above described first embodiment.

The fifth embodiment has the structure in which the fixing portion 20D prevents the pusher 19 from being detached from the protruding portion 1631. Therefore, the structure enables prevention of remanufacturing of the treatment tool by a person unrelated to a manufacturer that remanufactures the treatment tool.

Other Embodiments

Some embodiments of the disclosure have been described thus far, but the disclosure is not to be limited only to the above described first to fifth embodiments.

In each of the above described first to fifth embodiments, the treatment tool according to the disclosure is configured to apply both ultrasound energy and high frequency energy to a target site, but without being limited to this configuration, the treatment tool may be configured to apply at least one of ultrasound energy, high frequency energy, and thermal energy. "Applying thermal energy to a target site" herein means transmitting heat generated in a heater, for example, to a target site.

In each of the above described first to fifth embodiments, the inner pipe 14 is adopted as the tubular portion, but the tubular portion is not necessarily the inner pipe 14. The outer pipe 13 may be adopted as the tubular portion. That is, the jaw 11 may be configured to be opened and closed by movement of the outer pipe 13 along the central axis Ax.

In the above described first embodiment, the pusher 19 that is elastically deformable is adopted as the pusher, but without being limited to the pusher 19, any other fixation tool, such as a screw, may be adopted as the pusher.

In the above described first embodiment, the number of the pushers 19 adopted is just one, but without being limited to one, the number of the pushers may be plural. In a case where a plurality of the pushers is adopted, the pushers are respectively provided at positions where the pushers press the inner pipe 14 toward the central axis Ax.

In the above described first embodiment, the path heading from the opening 193 to the fitting recessed portion 194 in the pusher 19 is a linear path along the attachment direction Ar3, but the path is not limited to this linear path, and may be a curved path or an L-shaped path.

A treatment tool according to the disclosure enables improvement in ease of assembly.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment tool, comprising:
   an end effector configured to implement treatment of living tissue;
   an operation input portion configured to be operated by an operator;
   a tubular portion provided along a longitudinal axis of the treatment tool, the tubular portion having a first end and a second end, the first end being connected to the end effector, the second end being provided with a first engagement portion, wherein the first engagement portion is a notch;
   a driver configured to move along the longitudinal axis of the treatment tool responsive to operation of the operation input portion by the operator, the driver including a second engagement portion configured to engage with the first engagement portion, wherein the second engagement portion is a projection configured to engage with the notch of the first engagement portion;
   a pusher configured to connect the tubular portion and the driver to each other by coming into contact with the tubular portion toward a central axis of the tubular portion in a state where the first engagement portion and the second engagement portion have engaged with each other, wherein the pusher prevents movement of the central axis of the tubular portion to restrict movement of the tubular portion so that the notch of the first engagement portion is not disengaged from the projection of the second engagement portion; and
   an ultrasound transducer configured to generate ultrasound vibration, wherein a vibration transmission portion configured to transmit the ultrasound vibration generated by the ultrasound transducer is arranged in the tubular portion and the driver.

2. The treatment tool according to claim 1, wherein the pusher is configured to connect the tubular portion and the driver to each other responsive to the pusher pressing an outer peripheral surface of the tubular portion toward the central axis of the tubular portion.

3. The treatment tool according to claim 1, wherein the pusher is detachably attached to the driver.

4. The treatment tool according to claim 1, wherein the pusher is provided at a position across the tubular portion from the second engagement portion.

5. The treatment tool according to claim 1, wherein the first engagement portion is a notch provided in the tubular portion, and wherein the second engagement portion is a projection configured to fit in the notch.

6. The treatment tool according to claim 1, wherein the driver includes a protruding portion, and wherein the pusher is configured to be attached to the protruding portion.

7. The treatment tool according to claim 1, wherein the end effector is a jaw configured to open and close according to the operation on the operation input portion, the jaw being configured to grip the living tissue.

8. The treatment tool according to claim 1, further comprising:
   an elastic material provided between the operation input portion and the tubular portion, the elastic material being configured to transmit drive force according to the operation on the operation input portion, to the tubular portion.

9. The treatment tool according to claim 1, wherein the treatment tool is an ultrasound treatment tool, and wherein a vibration transmission portion configured to transmit ultrasound vibration is placed inside the tubular portion.

10. A treatment tool, comprising:
    an end effector configured to implement treatment of living tissue;
    an operation input portion configured to be operated by an operator;
    a tubular portion provided along a longitudinal axis of the treatment tool, the tubular portion having a first end and a second end, the first end being connected to the end effector, the second end being provided with a first engagement portion, wherein the first engagement portion is a notch;
    a driver configured to move along the longitudinal axis of the treatment tool responsive to operation of the operation input portion, the driver including a second engagement portion configured to engage with the first engagement portion, wherein the second engagement portion is a projection configured to engage with the notch of the first engagement portion;
    a pusher configured to connect the tubular portion and the driver to each other by coming into contact with the tubular portion toward a central axis of the tubular portion in a state where the first engagement portion and the second engagement portion have engaged with each other, the pusher including at least one of an attachment maintaining portion or a thin portion, the attachment maintaining portion being configured to restrict movement of the pusher in a first direction opposite to an attachment direction in which the pusher is attached to the driver, the thin portion being thinner than part of the pusher, the part being other than the thin portion, wherein the pusher prevents movement of the central axis of the tubular portion to restrict movement of the tubular portion so that the notch of the first engagement portion is not disengaged from the projection of the second engagement portion; and
    an ultrasound transducer configured to generate ultrasound vibration, wherein a vibration transmission portion configured to transmit the ultrasound vibration generated by the ultrasound transducer is arranged in the tubular portion and the driver.

11. The treatment tool according to claim 10, wherein the pusher is configured to connect the tubular portion and the driver to each other responsive to the pusher pressing on an outer peripheral surface of the tubular portion toward the central axis of the tubular portion.

12. The treatment tool according to claim 10, wherein the attachment maintaining portion includes a planar portion intersecting the first direction.

13. The treatment tool according to claim 10, wherein the pusher includes an opening into which part of the driver is inserted, and wherein the thin portion faces the opening.

14. A treatment tool, comprising:
- an end effector configured to implement treatment of living tissue;
- an operation input portion configured to be operated by an operator;
- a tubular portion provided along a longitudinal axis of the treatment tool, the tubular portion having a first end and a second end, the first end being connected to the end effector, the second end being provided with a first engagement portion, wherein the first engagement portion is a notch;
- a driver configured to move along the longitudinal axis of the treatment tool responsive to operation of the operation input portion, the driver including a second engagement portion configured to engage with the first engagement portion, wherein the second engagement portion is a projection configured to engage with the notch of the first engagement portion;
- a pusher configured to connect the tubular portion and the driver to each other by coming into contact with the tubular portion toward a central axis of the tubular portion in a state where the first engagement portion and the second engagement portion have engaged with each other, wherein the pusher prevents movement of the central axis of the tubular portion to restrict movement of the tubular portion so that the notch of the first engagement portion is not disengaged from the projection of the second engagement portion;
- a fixing portion configured to fix the pusher to the driver; and
- an ultrasound transducer configured to generate ultrasound vibration, wherein a vibration transmission portion configured to transmit the ultrasound vibration generated by the ultrasound transducer is arranged in the tubular portion and the driver.

15. The treatment tool according to claim 14, wherein the pusher is configured to connect the tubular portion and the driver to each other responsive to the pusher pressing on an outer peripheral surface of the tubular portion toward the central axis of the tubular portion.

16. The treatment tool according to claim 14, wherein the fixing portion is an adhesive.

17. The treatment tool according to claim 14, wherein the fixing portion is a pin.

18. The treatment tool according to claim 1, wherein the tubular portion includes a main body and an enlarged diameter portion that is connected to one end of the main body and has a diameter greater than a diameter of the main body, and the notch is provided in the enlarged diameter portion.

19. The treatment tool according to claim 1, wherein the second engagement portion of the driver has an arc-shaped tip.

* * * * *